US008728457B2

(12) United States Patent
Mummery

(10) Patent No.: US 8,728,457 B2
(45) Date of Patent: May 20, 2014

(54) METHODS OF INDUCING DIFFERENTIATION OF STEM CELLS

(76) Inventor: Christine Lindsay Mummery, Bilthoven (NL)

(*) Notice: Subject to any disclaimer, the term of this patent is extended or adjusted under 35 U.S.C. 154(b) by 1079 days.

(21) Appl. No.: 10/758,554

(22) Filed: Jan. 14, 2004

(65) Prior Publication Data
US 2005/0227353 A1 Oct. 13, 2005

Related U.S. Application Data

(63) Continuation of application No. PCT/AU02/00978, filed on Jul. 23, 2002.

(30) Foreign Application Priority Data

Jul. 24, 2001 (AU) ........................ PR6560
Mar. 18, 2002 (AU) ........................ PS1180

(51) Int. Cl.
A61K 48/00 (2006.01)
C12N 15/85 (2006.01)

(52) U.S. Cl.
USPC ........................ 424/93.1; 435/325

(58) Field of Classification Search
USPC .............. 800/8; 424/93.1; 435/325
See application file for complete search history.

(56) References Cited

U.S. PATENT DOCUMENTS 6,667,176 B1    12/2003  Funk et al.
7,425,448 B2    9/2008   Xu et al.
2002/0081724 A1* 6/2002  Carpenter et al. ............ 435/366

FOREIGN PATENT DOCUMENTS

AU    200222281          12/2000
IL    WO 00/70021    *   11/2000
WO    WO 99/53021        10/1999
WO    WO 01/34776 A1     5/2001
WO    WO 01/48151 A1     7/2001
WO    WO 02/14469 A2     2/2002

OTHER PUBLICATIONS

Wobus et al, (Roux's Arch Dev Biol, 204: 36-45, 1994.*
Wobus et al, (J Mol Cell Cardiol, 29: 1525-1539, 1997.*
Mummery et al, (Differentiation, 46: 51-60, 1991.*
Gearhart et al, WO 98/43679; Aug. 10, 1998.*
Mummery et al, Biochem Biophys Res Commun, 191(1): 188-195, 1993.*
Rohwedel et al, Dev Biol, 164(1): 87-101, 1994.*
Itskovitz-Eldor et al, (Molecular Medicine, 6(2): 88-95, 2000.*
Sugi et al, (Developmental Dynamics, 200: 155-162, 1994.*
Zhu et al, (Developmental Dynamics, 207: 429-438, 1996.*
Lough et al, (Developmental Dynamics, 217: 327-342, 2000.*
Klug et al, (J Clin Invest, 98: 216-224, 1996.*
Reubinoff et al (Nature Biotechnology, 18: 399-404, 2000).*
Skerjanc, (Trends Cardiovasc Med 1999;9:139-143, 1999).*
Amit et al (Developmental Biology, 227: 271-278, 2000).*
Rohwedel et al (Cells Tissues Organs, 165:190-202, 1999 (Abstract)).*
Eiges et al (Current Biology 2001, 11:514-518, 2001).*
Rohwedel et al (Cells Tissues Organs, 165: 190-202, 1999.*
Yu et al (Genes & Development, 22: 1987-1997, 2008).*
Xu et al (Circulation Research, 91: 501, 2002).*
Christine L. Mummery, et al. "Visceral-Endoderm-Like Cell Lines Induce Differentiation of Murine P19 Embryonal Carcinoma Cells", *Differentiation*, vol. 46, pp. 51-60 (1991).
A.J.M. van den Eijnden-van Raaij, et al., "Differentiation of Aggregated Murine P19 Embryonal Carcinoma Cells is Induced by a Novel Visceral Endoderm-Specific FGF-Like Factor and Inhibited by Activin A", *Mechanisms of Development*, vol. 33, pp. 157-166, (1991).
J. Rohwedel, et al., "Muscle Cell Differentiation of Embryonic Stem Cells Reflects Myogenesis in Vivo: Developmentally Regulated Expression of Myogenic Determination Genes and Functional Expression of Ionic Currents", *Developmental Biology*, vol. 164, pp. 87-101, (1994).
Michael A. Dyer, et al., "Indian Hedgehog Activities Hematopoiesis and Vasculogenesis and Can Respecify Prospective Neurectodermal Cell Fate in the Mouse Embryo", *Developmental*, vol. 128, pp. 1717-1730, (2001).
C. A. Eisenberg, et al., "Mixed Cultures of Avian Blastoderm Cells and the Quail Mesoderm Cell Line QCE-6 Provide Evidence for the Pluripotentiality of Early Mesoderm", *Developmental Biology*, 191; pp. 167-181 (1997), Article No. DB978718.
C. Mummery, et al., "Cardiomyocyte Differentiation of Mouse and Human Embryonic Stem Cells", *J. Anat.* 200, (2002), pp. 233-242.
Qi-Long Ying, et al., "Changing Potency by Spontaneous Fusion", *Nature*, vol. 416, Apr. 4, 2002; pp. 545-548.
S. L. Karp, et al., "Epithelial Differentiation of Metanephric Mesenchymal Cells After Stimulation with Hepatocyte Growth Factor or Embryonic Spinal Cord", *Proc. Natl. Acad. Sci., USA*, vol. 91, Developmental Biology, Jun. 1994; pp. 5286-5290.
Tsukasa Miyatake, et al., "Survival of Accommodated Cardiac Xenografts Upon Retransplantation Into Cyclosporine-Treated Recipients", *Transplantation*, vol. 65, No. 12, Jun. 27, 1998; pp. 1563-1569.
Van Meter, et al., "Methods" *The Journal of Thoracic and Cardiovascular Surgery*, vol. 110, No. 5, Nov. 1995; pp. 1443-1448.
Doetschman et al. The In Vitro Development of Blastocyst-derived embryonic stem cell lines: Formation of visceral yolk sac, blood islands and myocardium; J. Embryol. Exp. Morph. (1985) 87:27.
Johansson et al. Evidence for Improvement of Activin A and Bone Morphogenetic Protein 4 in Mammalian Mesoderm Development; Mol. and Cell Biol. (1995) 15:141.

(Continued)

*Primary Examiner* — Marcia S Noble
*Assistant Examiner* — Magdalene Sgagias
(74) *Attorney, Agent, or Firm* — E. Stewart Mittler

(57) ABSTRACT

The present invention relates to methods of inducing differentiation of stem cells. In particular, the invention relates to methods of inducing differentiation of embryonic stem cells into muscle cells or vascular endothelial cells. The invention also includes cells, cell lines, testing models and culture systems used in the methods of the present invention and differentiated cells produced therefrom. The present invention also provides methods of using the differentiated cells of the present invention for therapeutic purposes.

17 Claims, 11 Drawing Sheets

(56) References Cited

OTHER PUBLICATIONS

Kramer et al. Embryonic Stem Cell-derived Chondrogenic Differentiation in vitro: Activation by BMP-2 and BMP-4; Mech of Development (2000) 92:193.

Schuldiner et al. Effects of Eight Growth Factors on the Differentiation of Cells Derived from Human Embryonic Stem Cells; PNAS (2000) 97:11307.

Van Der Hayden et al. Twenty One Years of P19 Cells: What an Embryonal Carcinoma Cell Line Taught Us About Cardiomyocyte Differentiation; (2003) Cardiovascular Research 58:292.

Wobus et al. Retinoic Acid Accelerates Embryonic Stem Cell-Derived Cardiac Differentiation and Enhances Development of Ventricular Cardiomyocytes; (1997) J. Mol. Cell Cardiology 29:1525.

Wobus et al. Specific Effects of Nerve Growth Factor on the Differentiation Pattern of Mouse Embryonic Stem Cells In Vitro;(1988) Biomed Biochim Acta 12:965.

Xu et al. Characterization and Enrichment of Cardiomyocytes Derived from Human Embryonic Stem Cells (2002) Circulation Research 91:508.

Andrews, From teratocarcinomas to embryonic stem cells, Phil. Trans. R. Soc. Lond. B. (2002) 57:405.

Pera and Herzfeld, Differentiation of human pluripotent teratocarcinoma stem cells induced by bone morphogenic protein-2, Reprod. Fertil. Dev. (1998) 10:551.

Thomson, Embryonic stem cell lines derived from human blastocyts, Science (1998) 282:1145.

\* cited by examiner

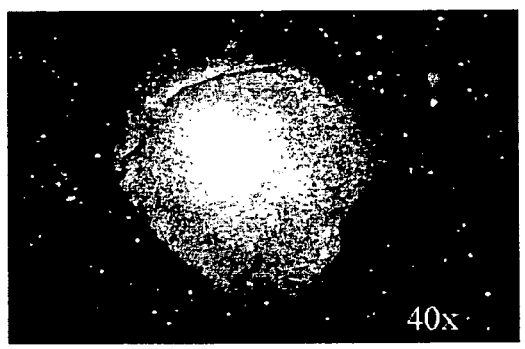 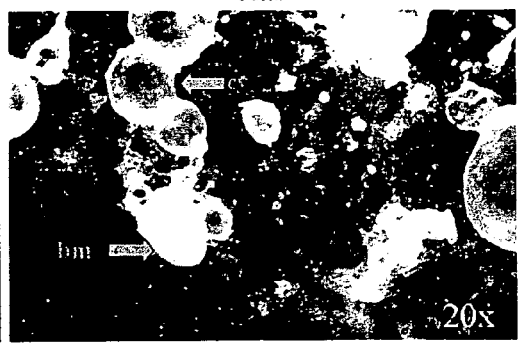
Fig. 1A                    Fig. 1B

METHODS OF INDUCING DIFFERENTIATION OF STEM CELLS

CROSS-REFERENCE TO RELATED APPLICATION

The present application is a continuation of PCT/AU02/00978, filed Jul. 23, 2002

The present invention relates to methods of inducing differentiation of stem cells. In particular, the invention relates to methods of inducing differentiation of embryonic stem cells into muscle cells or vascular endothelial cells. The invention also includes cells, cell lines, testing models and culture systems used in the methods of the present invention and differentiated cells produced therefrom. The present invention also provides methods of using the differentiated cells of the present invention for therapeutic purposes.

INTRODUCTION

Stem cells are undifferentiated cells which can give rise to a succession of mature functional cells. Embryonic stem (ES) cells are derived from the embryo and are pluripotent, thus possessing the capability of developing into any organ, cell type or tissue type. The process of differentiation in stem cells involves selective development of immature cells to committed and fully mature cells of various lineages. Derivatives of such lineages include, muscle, neural, skeletal, blood (hematopoietic), endothelial and epithelial cells. Differentiation of stem cells is known be triggered by various growth factors and regulatory molecules.

During differentiation the expression of stem cell specific genes and markers are often lost and cells acquire gene expression profiles of somatic cells or their precursors. In some cases, "master" genes have been described which control differentiation versus self-renewal.

Whilst differentiation of some lineage specific stem cells can be induced with a degree of certainty, a differentiation outcome of a population of pluripotent stem cells is less predictable. Placing the cells under conditions which induce specific cell types has been one form of an attempt to regulate the differentiation outcome. These conditions include growing the cells to high or low density, changing media, introducing or removing cytokines, hormones and growth factors, creating an environment which suits differentiation toward a specific cell type, such as providing a suitable substrate.

Generally, when a stem cell culture is induced to differentiate, the differentiated population is analysed for particular cell types by expression of genes, markers or phenotypic analysis. In any case, the respective cell types may then be selectively cultured to enrich their percentage population to eventually obtain a single cell type and culture.

The induction of a specific differentiated cell type can be useful for transplantation or drug screening and drug discovery in vitro. Methods of inducing differentiation in stem cells and muscle cells produced therefrom may be used for the study of cellular and molecular biology of tissue development, for the discovery of genes and proteins such as differentiation factors that play a role in tissue development and regeneration.

In particular, the induction of stem cells to differentiate into muscle cells (myocytes) is useful for muscle transplantation and therapeutic purposes, as well as providing potential human disease models in culture (e.g. for testing pharmaceuticals). The induction of cardiomyocyte differentiation in stem cells is especially useful in developing therapeutic methods and products for heart disease and abnormal heart conditions. However, the molecular pathways that lead to specification and terminal differentiation of specific cell types, such as myocytes, from embryonic stem cells during development are not entirely clear.

Therefore there remains a need for providing effective methods of inducing differentiation of stem cells into specific cell types, such as myocytes or endothelial cells.

SUMMARY OF THE INVENTION

In one aspect of the present invention there is provided a method of inducing differentiation of a stem cell, the method including:
culturing a stem cell in the presence of an embryonic cell and/or extracellular medium of an embryonic cell, under conditions that induce differentiation of the stem cell.

Preferably, the stem cell is an embryonic, human stem cell. More preferably, the stem cell is induced to differentiate into a myocyte (muscle cell), vascular endothelial cell or a haematopoietic cell. In the methods of the present invention as hereinbefore described, the embryonic cell is preferably derived from embryonic endoderm or ectoderm. More preferably, the embryonic cell is derived from extraembryonic tissue.

In the methods of the present invention the stem cell is preferably grown in the presence of an embryonic, endoderm cell and/or extracellular conditioned medium of an embryonic, endoderm cell to induce differentiation of the stem cell into a cardiomyocyte or a haematopoietic cell. More preferably, the stem cell is co-cultured in the presence of the embryonic cell. In the methods of the present invention the stem cell is preferably plated on a confluent monolayer of embryonic cells and allowed to grow in culture to induce differentiation of the stem cell.

Alternatively, the stem cell is grown in the presence of an embryonic, ectoderm cell and/or extracellular medium of an embryonic, ectoderm cell to induce differentiation of the stem cell into a skeletal muscle cell.

In yet another preferred embodiment, the stem cell is grown in the presence of an embryonic, ectoderm and/or endoderm cell, and/or extracellular medium of an embryonic, ectoderm and/or endoderm cell to induce differentiation of the stem cell into a vascular endothelial cell.

In a preferred aspect of the present invention there is provided a method of inducing muscle cell differentiation of a stem cell, the method including:
culturing a stem cell in the presence of an embryonic cell and/or extracellular medium of an embryonic cell, under conditions that induce differentiation of the stem cell into a muscle cell.

Preferably, the stem cell is grown in the presence of an embryonic, endoderm cell and/or extracellular medium of an embryonic, endoderm cell to induce differentiation of the stem cell into a cardiomyocyte (cardiac muscle cell). More, preferably the embryonic cell is extraembryonic. The embryonic cell is preferably derived from visceral endoderm, is a cell with visceral endoderm like properties or is derived from an embryonic cell line with characteristics of visceral endoderm. More preferably, the stem cell is co-cultured in the presence of the embryonic cell.

Alternatively, the stem cell is grown in the presence of an embryonic, ectoderm cell and/or extracellular medium of an embryonic, ectoderm cell to induce differentiation of the stem cell into a skeletal muscle cell. More preferably, the embryonic cell is derived from extraembryonic tissue.

Another aspect of the present invention is an embryonic cell for use in the methods of the present invention. Preferably, the embryonic cell is derived from embryonic or extraembryonic endoderm or ectoderm. Preferably, the embryonic cell is derived from visceral endoderm or is a cell with visceral endoderm like properties. More preferably, the embryonic cell is derived from a cell line with characteristics of visceral endoderm, such as the END-2 cell line (Mummery et al, 1985, *Dev Biol.* 109:402-410).

In a further preferred aspect of the present invention there is provided a method of inducing differentiation of a stem cell, the method including:

culturing a stem cell in the presence of a factor derived from an embryonic cell or extracellular medium of an embryonic cell under conditions that induce differentiation of the stem cell.

The present invention further provides an isolated factor that is secreted from an embryonic cell or is isolated from extracellular medium according to the present invention for use in a method of inducing differentiation of a stem cell.

In yet another aspect of the invention, there is provided a differentiated cell produced according to the methods as hereinbefore described. Preferably, the differentiated cell is a cardiomyocyte, skeletal muscle cell, vascular endothelial cell or a haematopoietic cell. The present invention also provides differentiated cells produced according to the methods of the invention that may be used for transplantation, cell therapy or gene therapy. Preferably, the invention provides a differentiated cell produced according to the methods of the invention that may be used for therapeutic purposes, such as in methods of restoring cardiac function in a subject suffering from a heart disease or condition.

Another aspect of the invention is a method of treating or preventing a cardiac disease or condition, the method including introducing an isolated cardiomyocyte cell and/or a cell capable of differentiating into a cardiomyocyte cell into cardiac tissue of a subject.

Preferably, the cardiomyocyte is produced by the differentiation of a stem cell according to methods as hereinbefore described. It is preferred that the subject is suffering from a cardiac disease or condition. In the method of the present invention, the isolated cardiomyocyte cell is preferably transplanted into damaged cardiac tissue of a subject. More preferably, the method results in the restoration of cardiac function in a subject.

In yet another preferred aspect of the invention there is provided a method of repairing cardiac tissue, the method including introducing an isolated cardiomyocyte cell and/or a cell capable of differentiating into a cardiomyocyte cell into damaged cardiac tissue of a subject.

Preferably, the cardiomyocyte is produced by the differentiation of a stem cell according to methods as hereinbefore described. It is preferred that the subject is suffering from a cardiac disease or condition. In the method of the present invention, the isolated cardiomyocyte cell is preferably transplanted into damaged cardiac tissue of a subject. More preferably, the method results in the restoration of cardiac function in a subject.

The invention also provides methods of treating vascular diseases and muscular diseases by transplanting differentiated to vascular endothelial cells or to skeletal muscle cells or progenitors of these cells.

The present invention preferably also provides a myocardial model for testing the ability of stem cells that have differentiated into cardiomyocytes to restore cardiac function.

The present invention further provides a cell composition including a differentiated cell produced by the method of the present invention, and a carrier.

FIGURES

FIG. 1A shows a phase contrast micrograph of human embryonic stem (hES) in co-culture with END-2 cells after a period of 13 days. The differentiated stem cells have mixed morphology but with a relatively high proportion of epithelial-like cells. The epithelial cells swell to fluid-filled cysts and between these cells are patches of cardiomyocytes. Cross section of the colony shown is about 2 mm (40× objective). Scale bar=100 µm.

FIG. 1B shows a phase contrast micrograph of human embryonic stem (hES) in co-culture with END-2 cells after a period of two to three weeks. Increasing patches of beating cardiac muscle cells (cardiomyocytes; bm) are present. The beating rate observed was approximately 60 beats per minute. (20× objective). Scale bar=100 µm.

FIG. 2 shows cells stained positively with α-actinin, confirming that they are indeed muscle cells. Scale bar=100 µm.

FIG. 3 shows co-cultures of stem cells with the mouse visceral endoderm-like cell line END-2. (a) P19 EC in normal monolayer culture, 3 days after initiation of co-culture with END-2 cells and after 10 days, when beating muscle (B.M.) is evident. (b) mES cell lineR1 in monolayer on its normal 'feeder' cells (SNL), 3 days after initiation of co-culture and 2 days later, when beating muscle is evident. (c) as (b), with the exception that B.M. is evident on day 7 after aggregation. (d) GCT27X human EC cell line on mouse embryonic fibroblast (MEF) feeder cells, 3 days after initiation of co-culture and after 16 days. No beating muscle is present. (e) hES cells on MEF feeders, 3 days after initiation of END-2 co-culture and beating muscle formed after 11 days.

FIG. 4 shows electrophysiological characteristics of cardiomyocytes from stem cells. Repetitive action potentials recorded from spontaneously beating areas. (a) In mouse P19 EC cell-derived cardiomyocytes. (b) In an aggregate of hES-derived cardiomyocytes. (c) Phase contrast image of the beating area in the hES culture from which the recording showed in (b) was derived. (Note the height of the protruding structure where the beating region is located, 20× objective.)

FIG. 5 shows isolated cardiomyocytes: (a) exhibiting sharp edges and well-defined sarcomeres in contrast with cells cultured for 2 days (b) which had disorganized sarcomeric patterning. (a) is a phase contrast image of multiple cells after isolation and fixation. (b) represents a single cell, digitally magnified 2× compared with (a).

FIG. 6 shows Immunocytochemistry on adult human primary atrial cardiomyocytes and stem cell-derived cardiomyocytes. Primary atrial cardiomyocytes stained positive for sarcomeric proteins including (green) α-actinin, (red) mlc-2a (a) and tropomyosin (b). Cell DNA was stained with (blue) Hoechst to distinguish normal and apoptotic cells. Cells cultured for 2 days had a disorganized tropomyosin sarcomeric patterning and diffuse antibody staining (c). mES-derived cardiomyocytes also show sharp banding when stained with α-actinin (d) but in hES-derived cardiomyocytes α-actinin is diffuse and poorly banded (not shown). (e) shows overall extensive α-actinin staining in hES-derived cardiomyocytes at low magnification.

FIG. 7 shows haemodynamic assessment of left ventricular function in mice. (a) Normal loop representing the relationship between volume and pressure changes in the mouse heart: indicated are the valvular events and stages during one cycle of contraction and relaxation. (b) Pressure volume relationship 4 weeks post-myocardial infarction: note the difference in the shape of the loop and the alterations in both contraction and relaxation.

Figure 2:
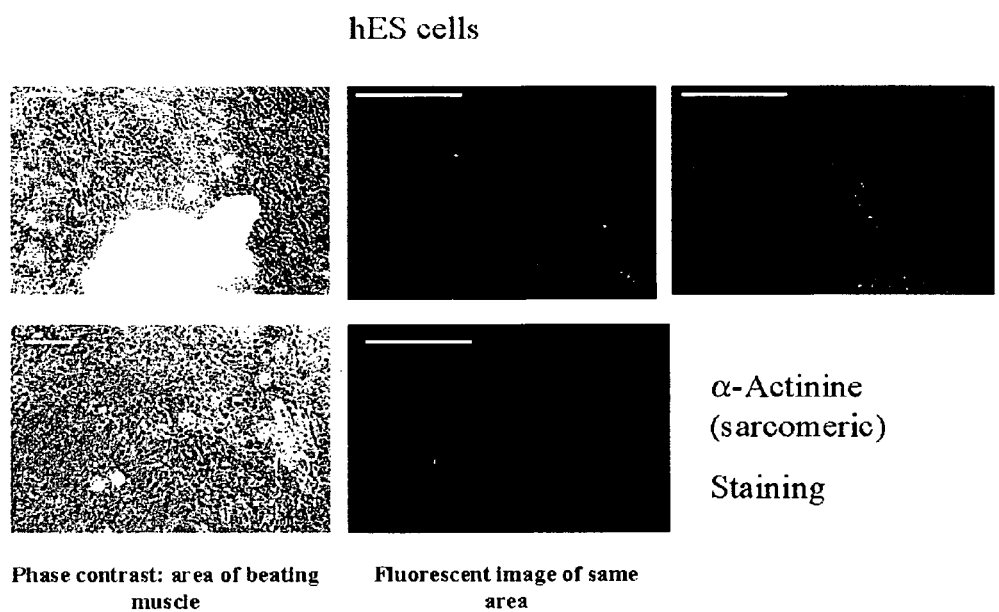

FIG. 10 shows effects of END-2 conditioned medium on P19 embryonal carcinoma cells. A. Induction of beating muscle in P19EC aggregates. Results from two independent clones (P19 EC and P19 clone 6 EC) on day 7 and 8 as indicated, are shown. All aggregates beat in the presence of DMSO on day 10. B. Northern blot showing induction of Brachyury T by END-2 conditioned medium in P19EC aggregates. DMSO also induces cardiomyocyte differentiation and is shown as a control. Both END-2 CM and DMSO induced Brachyury T expression are blocked by activin.

DETAILED DESCRIPTION OF THE INVENTION

In one aspect of the present invention there is provided a method of inducing differentiation of a stem cell, the method including:
    culturing a stem cell in the presence of an embryonic cell and/or extracellular medium of an embryonic cell, under conditions that induce differentiation of the stem cell.

Stem cells usually require co-culture with a fibroblast feeder layer to maintain their undifferentiated state. Those feeder layers that do not adequately maintain this state result in stem cells, loosing their undifferentiated characteristics to non-obvious phenotypes. Applicants have found that culturing stem cells with embryonic cells can provide a determining factor to the outcome of differentiated cells in culture. This control has never been seen with fibroblast cells.

The term "inducing differentiation of a stem cell" as used herein is taken to mean causing a stem cell to develop into a specific differentiated cell type as a result of a direct or intentional influence on the stem cell. Influencing factors that may induce differentiation in a stem cell can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density.

In the methods of the present invention a stem cell is undifferentiated prior to culturing and is any cell capable of undergoing differentiation. The stem cell may be selected from the group including, but not limited to, embryonic stem cells, pluripotent stem cells, haematopoietic stem cells, totipotent stem cells, mesenchymal stem cells, neural stem cells, or adult stem cells.

The stem cell is preferably a human embryonic stem cell which may be derived directly from an embryo or from a culture of embryonic stem cells. For example, the stem cell may be derived from a cell culture, such as human embryonic stem cells (hES) cells (Reubinoff et al., *Nature Biotech.* 16:399-404 2000). Whilst, the stem cell may be derived from other animals, they are most preferably human embryonic stem cells. The stem cell may be derived from an embryonic cell line or embryonic tissue. The embryonic stem cells may be cells which have been cultured and maintained in an undifferentiated state. Such cells have been described, in PCT/AU99/00990, PCT/AU00/01510, PCT/AU01/00735 and PCT/AU01/00278, the contents of which are incorporated herein by reference.

The stem cells suitable for use in the present methods may be derived from a patient's own tissue. This would enhance compatibility of differentiated tissue grafts derived from the stem cells with the patient. The stem cells may be genetically modified prior to use through introduction of genes that may control their state of differentiation prior to, during or after their exposure to the embryonic cell or extracellular medium from an embryonic cell. They may be genetically modified through introduction of vectors expressing a selectable marker under the control of a stem cell specific promoter such as Oct-4. The stem cells may be genetically modified at any stage with markers so that the markers are carried through to any stage of cultivation. The markers may be used to purify the differentiated or undifferentiated stem cell populations at any stage of cultivation.

The stem cell can be induced to differentiate into a cell type selected from the group including muscle cells, endothelial cells, such as vascular endothelial cells, epithelial cells, blood cells (haematopoietic cells) or neural cells. Preferably, the stem cell is induced to differentiate into a myocyte (muscle cell) or a vascular endothelial cell. More preferably, the stem cell is induced to differentiate into a cardiomyocyte or a skeletal muscle cell.

In a preferred embodiment of the present invention there is provided a method of inducing differentiation of a stem cell, the method including:
    culturing a stem cell in the presence of an embryonic cell under conditions that induce differentiation of the stem cell.

The embryonic cell used in the present method includes an embryonic cell derived from an embryo or a cell derived from extraembryonic tissue. The term "embryo" is defined as any stage after fertilisation up to 2 weeks post conception in mammals. It develops from repeated division of cells and includes the stages of a blastocyst stage which comprises an outer trophectoderm and an inner cell mass (ICM). The embryo may be an in vitro fertilised embryo or it may be an embryo derived by transfer of a somatic cell or cell nucleus into an enucleated oocyte preferably of human or non-human origin. Extraembryonic tissue includes cells produced by the embryo that make up the placenta.

In a preferred embodiment of the invention, the embryonic cell is derived from embryonic, preferably extraembryonic, endoderm or ectoderm. More preferably, the embryonic cell is derived from visceral endoderm tissue or visceral endoderm like tissue isolated from an embryo. Preferably visceral endoderm may be isolated from early postgastrulation embryos, such as mouse embryo (E7.5). Visceral endoderm or visceral endoderm like tissue can be isolated as described in Roelen et al, 1994 *Dev. Biol.* 166:716-728. Characteristically the visceral endoderm may be identified by expression of alphafetoprotein and cytokeratin ENDO-A). The embryonic cell may be an embryonal carcinoma cell, preferably one that has visceral endoderm properties.

The embryonic cell may be derived from a cell line or cells in culture. The embryonic cell may be derived from an embryonic cell line, preferably a cell line with characteristics of visceral endoderm, such as the END-2 cell line (Mummery et al, 1985, *Dev Biol.* 109:402-410). The END-2 cell line was established by cloning from a culture of P19 EC cells treated as aggregates in suspension (embryoid bodies) with retinoic acid then replated (Mummery et al, 1985, *Dev Biol.* 109:402-410). The END-2 cell line has characteristics of visceral endoderm (VE), expressing alpha-fetoprotein (AFP) and the cytoskeletal protein ENDO-A. Accordingly it is most preferred that the embryonic cell is derived from the END-2 cell line. These cell have been found to be particularly useful for inducing differentiation of a human stem cell to a cardiomyocyte (cardiac muscle cell).

The embryonic cell may be an ectoderm cell, which can be isolated according to methods described in Roelen et al 1994, *Dev. Biol.* 166:716-728. Ectoderm cells are known to express oct-4 and have alkaline phosphatase activity and, they also have SSEA-1 on their cell surface. Therefore, ectoderm cells can be identified and isolated based on the above characteristics. Ectoderm cells may secrete (growth) factors that induce differentiation to skeletal muscle or vascular endothelial cells. It is preferred that the ectoderm cells are derived from E7.5, embryonic mouse tissue.

Accordingly, in another aspect of the present invention there is provided an embryonic cell for use in the methods of the present invention. Preferably, the embryonic cell is derived from embryonic endoderm or ectoderm as discussed above.

In the present invention and methods as hereinbefore described, the stem cell and embryonic cell are cultured to induce differentiation into a specific cell type. Preferably, the stem cell and embryonic cell are co-cultured in vitro. This typically involves introducing the stem cell to an embryonic cell monolayer produced by proliferation of the embryonic cell in culture. Preferably, the embryonic cell monolayer is grown to substantial confluence and the stem cell is allowed to grow in the presence of extracellular medium of the embryonic cells for a period of time sufficient to induce differentiation of the stem cell to a specific cell type. Alternatively, the stem cell may be allowed to grow in culture containing the extracellular medium of the embryonic cell(s), but not in the presence of the embryonic cell(s). The embryonic cells and stem cells may be separated from each other by a filter or an acellular matrix such as agar.

In the methods of the present invention the stem cell is preferably plated on a monolayer of embryonic cells and allowed to grow in culture to induce differentiation of the stem cell. More preferably, the monolayer is confluent and is mitogenically inactive.

Conditions for obtaining differentiated embryonic stem cells are those which are non-permissive for stem cell renewal, but do not kill stem cells or drive them to differentiate exclusively into extraembryonic lineages. A gradual withdrawal from optimal conditions for stem cell growth favours differentiation of the stem cell to specific cell types. Suitable culture conditions may include the addition of DMSO, retinoic acid, FGFs or BMPs in co-culture which could increase differentiation rate and/or efficiency.

The cell density of the embryonic cell layer affects its stability and performance. The embryonic cells should preferably be confluent. More preferably, the embryonic cells are grown to confluence and are then exposed to an agent which prevents further division of the cells, such as mitomycin C. The embryonic monolayer layer is preferably established 2 days prior to addition of the stem cell(s). The stem cells are preferably dispersed and then introduced to a monolayer of embryonic cells. More preferably, the stem cells and embryonic cells are co-cultured for a period of two to three weeks until a substantial portion of the stem cells have differentiated. Preferably, the stem cell is induced to differentiate into a myocyte (muscle cell) including cardiomyocytes and skeletal muscle cells, a vascular endothelial cell or a haematopoietic cell. It is preferred that the embryonic cell is derived from extraembryonic tissue and more preferably from embryonic endoderm or ectoderm.

In another preferred embodiment of the present invention there is provided a method of inducing differentiation of a stem cell, the method including:

culturing a stem cell in the presence of extracellular medium of an embryonic cell under conditions that induce differentiation of the stem cell.

The term "extracellular medium of an embryonic cell" as used herein is taken to mean conditioned medium produced from growing an embryonic cell as herein described in a medium for a period of time so that extracellular factors, such as secreted proteins, produced by the embryonic cell are present in the conditioned medium. The medium can include components that encourage the growth of the cells, for example basal medium such as Dulbecco's minimum essential medium, Ham's F12, or foetal calf serum.

In an even further preferred aspect of the present invention there is provided a method of inducing differentiation of a stem cell, the method including:

culturing a stem cell in the presence of a factor derived from an embryonic cell or extracellular medium of an embryonic cell under conditions that induce differentiation of the stem cell.

The extracellular medium preferably includes cellular factors, such as secreted proteins, that are capable of inducing differentiation of a stem cell. Such secreted proteins will typically bind receptors on a cell surface to trigger intracellular pathways which can initiate differentiation of the cell. Examples of suitable extracellular factors include Ihh and BMP2 as described in Dyer et al 2001, *Dev.* 128:1717-1730.

In another aspect of the present there is provided an isolated factor that is secreted from an embryonic cell or isolated from extracellular medium according to the present invention for use in a method of inducing differentiation of a stem cell. Suitable isolated factors may be selected by their ability to induce differentiation of a stem cell. For example, culture cell assay systems can be used to identify protein fractions and specific factors that are capable of inducing differentiation of a stem cell. The factors may include secreted proteins that are present in the extracellular medium of an embryonic cell. Suitable proteins may be extracted and purified by conventional methods known to those skilled in the field.

In another preferred aspect of the present invention there is provided a method of inducing muscle cell differentiation of a stem cell, the method including:

culturing a stem cell in the presence of an embryonic cell and/or extracellular medium of an embryonic cell, under conditions that induce differentiation of the stem cell into a muscle cell.

In a preferred embodiment the stem cell is induced to differentiate in to a cardiomyocyte cell. The applicants have found that culturing the stem cell with embryonic, preferably extraembryonic, endoderm cells causes a preferential induction of differentiation toward specific cell types, in particular toward muscle cells. It is most preferred that this combination of stem cell and embryonic endoderm cells induces differentiation toward cardiomyocytes. It is preferred that the stem cell is human, preferably a human embryonic stem cell (hES). More preferably, the stem cell is co-cultured with the embryonic cell. This is typically achieved by introducing dispersed stem cells to a culture medium with a monolayer of suitable embryonic cells. More preferably, the monolayer is of confluent embryonic cells.

In an even further preferred embodiment the embryonic cell is an endoderm cell derived from visceral endoderm or is an embryonic cell with visceral endoderm properties. More preferably, the visceral endoderm cells are derived from E7.5 mouse embryo. The embryonic cell may be an embryonal carcinoma cell, preferably one that has visceral endoderm properties. More preferably, the embryonic cell is derived from a cell line or cells in culture. The embryonic cell may be derived from an embryonic cell line, preferably a cell line with characteristics of visceral endoderm, such as the END-2 cell line (Mummery et al, 1985, Dev Biol. 109:402-410). More, preferably the embryonic cell is derived from extraembryonic tissue and more preferably is derived from visceral endoderm. Endoderm cells are typically adjacent to sites of heart formation in vertebrates. In individuals where endoderm differentiation is defective or absent, the heart develops abnormally.

In order to induce differentiation of the stem cell to a cardiomyocyte it is preferable to introduce the stem cell to an extraembryonic, endoderm cell monolayer in culture. The monolayer is produced by proliferation of the embryonic cell derived from embryonic endoderm, more preferably extraembryonic endoderm. The embryonic endoderm is preferably extraembryonic, visceral endoderm. More preferably, the cell monolayer is produced by END-2 cells. It is preferred that the embryonic cells are cultured and passaged before allowing them to grow to form a monolayer. The monolayer is preferably grown to confluence in a suitable medium, such as DMEM or M16 medium. The monolayer may then be treated with certain agents to prevent further division of the cells. For instance, the monolayer can be treated with mitomycin and then the stem cell can be plated on the mitogenically inactive monolayers.

The stem cells are allowed to grow in the presence of extracellular medium of the endoderm cells for a period of time sufficient to induce differentiation of the stem cell to a cardiomyocyte, that is most preferably beating. Most preferably, the co-culturing is carried out for about two to three weeks and the medium is preferably replaced regularly such as every 5 to 6 days with fresh medium.

Alternatively, the stem cell may be allowed to grow in culture containing the extracellular medium of the endoderm cells, but not in the presence of the endoderm cells. Therefore, the stem cell may be grown in the presence of extracellular medium of an embryonic, endoderm cell to induce differentiation of the stem cell into a muscle cell such as a cardiomyocyte (cardiac muscle cell).

In the methods of the present invention the cardiomyocyte cells produced are preferably beating. Cardiomyocytes are a differentiated cell type derived from stem cells. Muscle cells, including cardiomyocytes, can be fixed and stained with α-actinin antibodies to confirm muscle phenotype. α-troponin, α-tropomysin and α-MHC antibodies also give characteristic muscle staining. Preferably, the cardiomyocytes are fixed according to methods known to those skilled in the art. More preferably, the cardiomyocytes are fixed with paraformaldehyde, preferably with about 2% to about 4% paraformaldehyde. Ion channel characteristics and action potentials of muscle cells can be determined by patch clamp, electrophysiology and RT-PCR.

Stem cells from which cardiomyocytes are to be derived can be genetically modified to bear mutations in, for example, ion channels (this causes sudden death in humans). Cardiomyocytes derived from these modified stem cells will thus be abnormal and yield a culture model for cardiac ailments associated with defective ion channels. This would be useful for basic research and for testing pharmaceuticals. Likewise, models in culture for other genetically based cardiac diseases could be created. Cardiomyocytes produced in the present methods can also be used for transplantation and restoration of heart function.

For instance, Ischaemic heart disease is the leading cause of morbidity and mortality in the western world. Cardiac ischaemia caused by oxygen deprivation and subsequent oxygen reperfusion initiates irreversible cell damage, eventually leading to widespread cell death and loss of function. Strategies to regenerate damaged cardiac tissue by cardiomyocyte transplantation may prevent or limit post-infarction cardiac failure. The methods of inducing stem cells to differentiate into cardiomyocytes, as hereinbefore described would be useful for treating such heart diseases. Cardiomyocytes produced by the present methods may also be used in a myocardial infarction model for testing the ability to restore cardiac function.

The present invention preferably provides a myocardial model for testing the ability of stems cells that have differentiated into cardiomyocytes to restore cardiac function. In order to test the effectiveness of cardiomyocyte transplantation in vivo, it is important to have a reproducible animal model with a measurable parameter of cardiac function. The parameters used should clearly distinguish control and experimental animals (see for example Palmen et al. (2001), Cardiovasc. Res. 50, 516-524) so that the effects of transplantation can be adequately determined. PV relationships are a measure of the pumping capacity of the heart and may be used as a read-out of altered cardiac function following transplantation.

A host animal, such as but not limited to, an immunodeficient mouse may be used as a 'universal acceptor' of cardiomyocytes from various sources. Preferably, the cardiomyocytes are produced by the method of the present invention.

The myocardial model of the present invention is preferably designed to assess the extent of cardiac repair following transplant of cardiomyocytes or suitable progenitors into a suitable host animal. More preferably, the host animal is an immunodeficient animal created as a model of cardiac muscle degeneration following infarct that is used as a universal acceptor of the differentiated cardiomyocytes. This animal can be any species including but not limited to murine, ovine, bovine, canine, porcine and any non-human primates. Parameters used to measure cardiac repair in these animals may include, but are not limited to, electrophysiological characteristic of heart tissue or various heart function. For instance, contractile function may be assessed in terms of volume and pressure changes in a heart. Preferably, ventricular contractile function is assessed. Methods of assessing heart function and cardiac tissue characteristics would involve techniques also known to those skilled in the field.

In another aspect of the invention there is provided a method of treating or preventing a cardiac disease or condition in a patient, the method including introducing a cardiomyocyte cell and/or a cardiomyocyte progenitor or a cell capable of differentiating into a cardiomyocyte into cardiac tissue of a patient.

The term "treating or preventing" as used herein means alleviating or reducing the symptoms of the condition that is being treated or prevented.

Preferably, the cardiomyocyte is produced by the differentiation of a stem cell according to methods as hereinbefore described. It is preferred that the subject is suffering from a cardiac disease or condition. In the method of the present invention, the isolated cardiomyocyte cell is preferably transplanted into damaged cardiac tissue of a subject. More preferably, the method results in the restoration of cardiac function in a subject.

A "cell that is capable of differentiating into a cardiomyocyte" or a cardiomyoctye progenitor may include a stem cell that has been co-cultured with visceral endoderm and/or extracellular medium of visceral endoderm but has not completed differentiation toward the cardiomyocyte.

Suitable cardiac diseases may include, but are not limited to cardiac infarction or cardiac hypertrophy.

In yet another preferred aspect of the invention there is provided a method of repairing damaged cardiac tissue, the method including introducing a cardiomyocyte cell and/or a cardiomyocyte progenitor or a cell capable of differentiating into a cardiomyocyte into the damaged cardiac tissue of a subject.

Preferably, the cardiomyocyte is produced by the differentiation of a stem cell according to methods as hereinbefore described. It is preferred that the subject is suffering from a cardiac disease or condition. In the method of the present invention, the isolated cardiomyocyte cell is preferably transplanted into damaged cardiac tissue of a subject. More preferably, the method results in the restoration of cardiac function in a subject.

Damaged skeletal muscle tissue may result from muscular dystrophy.

In yet another preferred aspect there is provided a method of inducing differentiation of a stem cell to a skeletal muscle cell, the method including:

culturing a stem cell in the presence of an embryonic ectoderm cell and/or extracellular medium of an embryonic ectoderm cell, under conditions that induce differentiation of the stem cell into a skeletal muscle cell.

Ectoderm cells can be isolated according to methods described in Roelen et al 1994, *Dev. Biol.* 166:716-728. Ectoderm cells are known to express oct-4 and have alkaline phosphatase activity and they also have SSEA-1 on their cell surface. Therefore, ectoderm cells can be identified and isolated based on the above characteristics. Ectoderm cells may secrete (growth) factors that induce differentiation to skeletal muscle. It is preferred that the ectoderm cells are derived from E7.5, embryonic mouse tissue. More preferably, the ectoderm cells are co-cultured with the stem cells using similar methods as discussed earlier. An ectoderm monolayer is preferably established in culture and preferably dispersed stem cells are introduced to the culture for a period of time sufficient to induce differentiation of the stem cells to skeletal muscle cells.

Skeletal muscle cells are typically elongated, multinucleate cells that "twitch" and express MF20. When skeletal muscle cells are stained with α-actinin they normally produce a striped staining pattern. Skeletal muscle cells produced by the methods of the present invention can be used for transplantation in the treatment of muscle disease.

In another aspect of the invention there is provided a method of a method of treating or preventing muscle disease in a patient, said method comprising:

introducing to the muscle of the patient, a skeletal muscle cell and/or a skeletal muscle cell progenitor that has been co-cultured in the presence of embryonic ectoderm cells and/or extracellular medium of embryonic ectoderm cells.

Preferably, the skeletal muscle cells have been differentiated from a stem cell co-cultured under the conditions described above.

Muscle disease may be due to muscular dystrophy. However, the method of treatment may be applicable to any condition that requires regeneration and renewal of muscle cells.

In yet another preferred aspect there is provided a method of inducing differentiation of a stem cell to a vascular endothelial cell, the method including:

culturing a stem cell in the presence of an embryonic ectoderm and/or endoderm cell, and/or extracellular medium of an embryonic, ectoderm and/or endoderm cell to induce differentiation of the stem cell into a vascular endothelial cell.

More, preferably the embryonic cell is derived from extraembryonic ectoderm and/or endoderm tissue. Preferably, embryonic tissue is derived form embryonic E7.5 mouse. The embryonic ectoderm or endoderm cell may be obtained as previously discussed. The first vascular network in the embryo forms adjacent to visceral extraembryonic endoderm in the yolk sac, which produce factors affecting endothelial cells like TGFβ and VEGF. Therefore, more preferably the embryonic cell used in the above method is derived from visceral extraembryonic endoderm or is a cell with visceral cell like properties. The embryonic endoderm and/or ectoderm cell is preferably co-cultured with the stem cell using methods previously discussed. However, VEGF may be added to the culture medium to promote vascular endothelial cell growth in culture.

Vascular endothelial cells produced by the method of the invention can be identified by being capable of forming vascular networks sometimes containing blood. The vascular endothelial cells typically express receptors for VEGF, stain for PE-CAM, VE-CAM and von Willebrand factor. The vascular endothelial cells produced by the methods of the present invention would be useful as models for genetically based vascular disease. An example could be human hereditary telangiectasia, where patients have mutations in TGF-β receptors and a chronic bleeding syndrome. It is difficult to isolate and maintain long-term cells from patients with this disease to understand the pathology. Therefore, genetically modified stem cells induced to differentiate to vascular endothelial cells can provide a useful culture model. In addition, the vascular endothelial cells produced by the present methods can be used for transplantation and/or a route for delivery of gene therapy.

In another aspect of the present invention there is provided a method of treating or preventing a vascular disease in vascular tissue, said method comprising:

introducing to the vascular tissue, a vascular endothelial cell and/or a vascular endothelial progenitor cell that has been co-cultured in the presence of an embryonic ectoderm and/or endoderm cell and/or extracellular medium of an embryonic ectoderm and/or endoderm cell.

Preferably the vascular endothelial cells have been differentiated from a stem cell co-cultured under conditions described above.

Preferably, the vascular disease is caused by any one of hereditary hemorrhagic telangiectasia, vascular deterioration as a result of diabetes, or smoking.

In yet another aspect of the invention, there is provided a differentiated cell produced according to the methods as hereinbefore described. Preferably, the differentiated cell is a cardiomyocyte, skeletal muscle cell, vascular endothelial cell or a haematopoietic cell. The present invention also provides differentiated cells produced according to the methods of the invention that may be used for transplantation, cell therapy or gene therapy. Preferably, the invention provides a differentiated cell produced according to the methods of the invention that may be used for therapeutic purposes, such as in methods of restoring cardiac function in a subject suffering from a heart disease or condition.

The differentiated cells may be used as a source for isolation or identification of novel gene products including but not limited to growth factors, differentiation factors or factors controlling tissue regeneration, or they may be used for the generation of antibodies against novel epitopes.

The differentiated cells produced according to the methods of the present invention may be clonally expanded. A specific differentiated cell type can be selectively cultivated from a mixture of other cell types and subsequently propagated. Specific differentiated cell types that are clonally expanded can be useful for various applications such as the production of sufficient cells for transplantation therapy, for the production of sufficient RNA for gene discovery studies etc. The differentiated cells may be used to establish cell lines according to conventional methods.

The differentiated cells produced according to the methods of the present invention may be genetically modified. For instance, a genetic construct may be inserted to a differentiated cell at any stage of cultivation. The genetically modified cell may be used after transplantation to carry and express genes in target organs in the course of gene therapy.

The differentiated cells produced according to the methods of the present invention may be preserved or maintained by any methods suitable for storage of biological material. Effective preservation of differentiated cells is highly important as it allows for continued storage of the cells for multiple future usage. Traditional slow freezing methods, commonly utilised for the cryo-preservation of cell lines, may be used to cryo-preserve differentiated cells.

The present invention further provides a cell composition including a differentiated cell produced by the method of the present invention, and a carrier. The carrier may be any physiologically acceptable carrier that maintains the cells. It may be PBS or other minimum essential medium known to those skilled in the field. The cell composition of the present invention can be used for biological analysis or medical purposes, such as transplantation.

The cell composition of the present invention can be used in methods of repairing or treating diseases or conditions, such as cardiac disease or where tissue damage has occurred. The treatment may include, but is not limited to, the administration of cells or cell compositions (either as partly or fully differentiated) into patients. These cells or cell compositions would result in reversal of the condition via the restoration of function as previously disclosed above through the use of animal models.

Throughout the description and claims of this specification, the word "comprise" and variations of the word, such as "comprising" and "comprises", is not intended to exclude other additives, components, integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

The present invention will now be more fully described with reference to the accompanying examples and drawings. It should be understood, however that the description following is illustrative only and should not be taken in any way as a restriction on the generality of the invention described above.

EXAMPLES

Example 1

Differentiation of Human Embryonic Stem (hES) Cells into Cardiomyocytes (a) Co-Culturing of hES Cells With END-2 Cells Human embryonic stem cells (hES cells) Reubinoff et al, *Nature Biotech.* 16:399-404) were co-cultured with END-2 cells ((Mummery et al, 1985, *Dev Biol.* 109:402-410)). The END-2 cells are grown routinely in a 1:1 ratio of Dulbecco's minimum essential medium (DMEM) and Ham's F12 medium (DF) with 7.5% FCS. Cells were then passaged twice weekly, 1:5 using trypsin/EDTA (0.125% w/v; 50 mM resp). The hES cells were cultured in DMEM with 20% FCS, 0.1 mM β-mrcaptoethanol, 1% non-essential amino acids, 2 mM glutamine plus antibiotics (pen/strep) on mitomycin (10 µg/ml) treated embryonic feeder cells. HES were subcultured by treating with dispase and mechanical slicing of individual colonies into 6-10 pieces followed by transfer of the pieces to new feeder cells.

To initiate co-cultures, confluent cultures of END-2 cells were first passaged 1:10 on to gelatin-coated glass coverslips or tissue culture plastic wells in DMEM with 7.5% FCS and grown for 3 days to confluency. Monolayers were then treated with 10 µg/ml mitomycin C for 3 hours, washed 3 times in phosphate-buffered saline (PBS) without $Ca^{2+}$ and $Mg^{2+}$, and hES medium added. The hES cells were then dispersed using 10 mg/ml dispase for 3-5 minutes, followed by gentle agitation in a pipette to yield a suspension containing small cell clumps of approximately 10-50 cells. These suspensions were then plated on the mitogenically inactive END-2 monolayers, for 2-3 weeks, in hES complete medium. The medium was replaced every 5-6 days with fresh hES medium.

(b) Co-Culturing of hES Cells With Visceral Endoderm Cells

Visceral endoderm cells were isolated from the three germ layers of gastrulating mouse embryos at E7.5 (where E0.5 is noon on the day of the vaginal plug, as described previously using dispase (Roelen et al, 1994, *Dev. Biol.* 166:716-728). The separated germ layers were plated on to poly-L-lysine coated culture dishes in M16 medium and allowed to attach overnight. The next day, M16 was replaced by hES complete medium, and on day 3 after germ cell isolation, pieces of undifferentiated cell "transfers" were plated on to the attached endodermal and ectodermal cell from the mouse embryo. Cultures were then grown for 2 to 3 weeks and medium refreshed every 5-6 days.

(c) Analysis of Co-Culture Experiments (a) and (b)

The cultures described in (a) and (b) above were scored for the presence of areas of beating muscle from 10 days onwards.

(i) Immunofluorescence.

The cultures were then fixed after areas of beating muscle became evident in 2% paraformaldehyde for 30 min, washed 3 times and stored in PBS until use. The cultures were then stained to verify the muscle phenotype using α-actinin antibodies (monoclonal anti-α-actinin (sarcomeric) clone EA-53, dilution 1:1000, Sigma; secondary antibody: goat antimouse-IgG-Cy3).

(d) Results of Co-Culture Experiments (a) and (b)

(i) hES—END-2 co-culture.

During the first week of co-culture, the clumps of cells gradually spread and differentiate to cells with mixed morphology but with a relatively high proportion of epithelial-like cells. By the second week, these swell to fluid-filled cysts (see FIG. 1A). Between these, distinct patches of cells become evident which begin to beat a few days later. Between 12 and 21 days, increasingly more of these beating patches appear. There is no apparent difference between glass and tissue culture substrates, both yielding beating muscle as demonstrated in 3 independent experiments that indicated 15-20% of the wells containing one or more areas of beating muscle. Beating rate is approximately 60 beats per minute and highly temperature sensitive. These cells stain positively with α-actinin, confirming that they are indeed muscle cells (FIG. 2).

(ii) hES—E7.5 endoderm co-culture.

During the first week of culture, the hES pieces placed on top of the endoderm gradually begin to spread and flatten and on day 12, the first areas of beating muscle cells become evident. This is not accompanied by the extensive cyst formation observed in the END-2 co-cultures but areas resembling vascular endothelial cell networks do appear at the edges of the culture.

Example 2

Differentiation of Human Embryonic Stem (hES) Cells into Skeletal Muscle Cells

Human stem cells (hES) as used in Example 1 were placed on ectoderm isolated from E7.5 day embryos (E0.5 is day of plug). With sharpened tweezers and tungsten needles, the embryos were prepared out of the decidua and kept on ice in HEPES-buffered DMEM containing 10% FCS. After removing Reichert's membrane, the embryonic and extraembryonic parts of the conceptus were separated with tungsten needles. The node and primitive streak were removed and the embryonic part incubated in 2.5% pancreatin and 0.5% trypsin in PBS on ice for 8 min. After incubation, the embryos were transferred to HEPES-buffered DMEM containing 10% FCS on ice. The ectoderm, endoderm and mesoderm could then be cleanly isolated using tungsten needles.

The hES cells initially resemble those on endoderm but by day 18 there are areas of highly elongated, twitching cells that resemble skeletal muscle. There are no areas reminiscent of beating cardiac muscle although vascular networks (Vascular endothelial cells) are evident.

Example 3

Differentiation of Human Embryonic Stem (hES) Cells into Vascular Endothelial Cells Human stem cells (hES) as used in Example 1 were placed on ectoderm and/or endoderm cells. Co-culture condition of hES with ectoderm or endoderm were as above. Vascular endothelial cells in networks accompanied differentiation to other somatic cell types.

Example 4

Co-Culture of Visceral Endoderm Cells and hES and Differentiated Cardiomyocytes a) Co-Culture END-2 cells, P19 EC, hEC and hES cells were cultured as described previously (Mummery et al. 1985, 1991; vanden Eijnden-van Raaij et al. 1991; Slager et al. 1993; Reubinof et al. 2000). The hES2 cell line from ESI (Reubinof et al. 2000) was used in all experiments. To initiate co-cultures, mitogenically inactive END-2 cell cultures, treated for 1 h with mitomycin C (10 μg ml$^{-1}$) as described in Example 1, replaced mouse embryonic fibroblasts (MEFs) as feeders for hEC, mES and hES. Co-cultures with P19EC, which are feeder independent, were initiated and maintained as described previously (Mummery et al. 1991). Cultures were then grown for 2-3 weeks and scored for the presence of areas of beating muscle from 5 days onwards.

(b) Isolation of Primary Human Adult Cardiac Cells

Human atrial cells from surgical biopsies served as a control for antibody staining, electrophysiology and characterization of ion channels by RT-PCR. Cardiac tissue was obtained with consent from patients undergoing cardiac surgery. Atrial appendages routinely removed during surgery were immediately transferred to ice cold Krebs-Ringer (KR) saline solution. Tissues were trimmed of excess connective and adipose tissue and washed twice with sterile. KR solution. Myocardial tissue was minced with sterile scissors, then dissociated to release individual cells by a three-step enzymatic isolation procedure using published methods (Peeters et al. (1995), Am. J. Physiol. 268, H1757-H1764) The first step involved a 15-min incubation with 4.0 U mL$^{-1}$ protease type XXIV (Sigma, St Louis, Mo., USA) at 37° C. Tissues were then transferred to a solution consisting of collagenase 1.0 mg mL$^{-1}$ and hyaluronidase 0.5 mg mL$^{-1}$, followed by three further incubations with collagenase (1.0 mg mL$^{-1}$) for 20 min each at 37° C. Tissue extracts were combined and the calcium concentration restored to 1.79 mmol L$^{-1}$. Cardiomyocytes were transferred to tissue culture medium M199 enriched with 10% FBS, penicillin (100 U mL$^{-1}$)/streptomyocin (100 μg mL$^{-1}$), 2.0 mmol L$^{-1}$ L-carnitine, 5.0 mmol L$^{-1}$ creatine, 5.0 mmol L$^{-1}$ taurine and seeded directly on to glass cover-slips coated with 50 μg mL$^{-1}$ poly L-lysine and cultured overnight.

(c) Immunocytochemistry

Attached primary cardiomyocytes, mES (E14 and R1) and hES-derived cardiomyocytes were fixed with 3.0% paraformaldehyde in PBS with Ca$^{2+}$ and Mg$^{2+}$ for 30 min at room temperature, then permeabilized with 0.1% triton X 100 in PBS for 4 min. Immunocytochemistry was performed by standard methods using monoclonal antibodies directed against sarcomeric proteins including α-actinin and tropomyosin (Sigma). Antibodies specific for isoforms of myosin light chain (MLC2a/2v) were used to distinguish between atrial and ventricular cells (gift of Dr Ken Chien) (Table 1). Secondary antibodies were from Jackson Immunoresearch Laboratories. Cultured cardiac fibroblasts served as a negative control for sarcomeric proteins and cells were visualized using a Zeiss Axiovert 135M epifluorescence microscope (Carl Zeiss, Jena GmbH, Germany). Images were pseudocoloured using image processing software.

TABLE 1

Antibodies used to stain atria cardiomyocytes

| Primary antibody | Dilution | Secondary antibody | Dilution |
|---|---|---|---|
| Mouse anti-α-actinin IgG | 1:800 | Goat anti-mouse IgG-cy3/FITC conjugated | 1:250 |
| Mouse anti-tropomyosin IgG | 1:50 | Goat anti-mouse IgG-cy3 conjugated | 1:250 |
| Polyclonal rabbit anti-mouse mic-2a (atrial) | 1:500 | Goat anti-rabbit IgG-cy3 conjugated | 1:250 |
| Hoechst (nucleic acid) | 1:500 | | |

(d) Semi-Quantitative RT-PCR for Ion Channel Expression

P19EC cells were differentiated into beating muscle by the aggregation protocol in the presence of 1% dimethyl sulphoxide (Rudnicki & McBurney, 1987). After 16 days in these culture conditions, beating areas were excised and RNA was isolated using Trizol (Gibco) and reversed transcribed using M-MLV-RT (Gibco). Primers for cardiac actin (Lanson et al. (1992) Circulation 85, 1835-1841), MLC2v (Meyer et al. (2000) FEBS Lett, 478, 151-158), ERG (Lees-Miller et al. (1997), Circ. Res. 81, 719-726) and Kir2.1 (Vandorpe et al. (1998), J. Biol. Chem. 273, 21542-21553) were used as described previously. Primers for mouse L-type calcium channel subunit α1c (sense 5-CCAGATGAGACCCG-CAGCGTAA; antisense 5'-GTCTGCGGCGTTCTC-CATCTC; GenBank accession no. L01776; product size 745 bp), Scn5a (sense 5'-CTTGGCCAAGATCAACCTGCTCT; antisense 5'-CGGACAGGGCCAAATACTCAATG; AJ271477; 770 bp) and β-tubulin (sense 5-TCACTGTGC-CTGAACTTACC; antisense 5'-GAACATAGCCG-TAAACTGC; X04663; 319 bp) were designed using Vector NTI software (InforMax, North Bethesda, Md., USA).

(e) Patchclamp Electrophysiology

Experiments were performed at 33° C., using the whole cell voltage clamp configuration of the patch-clamp technique. After establishment of the gig a seal the action potentials were measured in the current clamp mode. The data were recorded from cells in spontaneously beating areas using an Axopatch 200B amplifier (Axon Instruments Inc., Foster City, Calif., USA). Output signals were digitized at 2 kHz using a Pentium III equipped with an AD/DAC LAB PC+ acquisition board. (National Instruments, Austin, Tex., USA). Patch pipettes with a resistance between 2 and 4 M Ω were used. Composition of the bathing medium was 140 mM NaCl, 5 mM KCl, 2 mM $CaCl_2$, 10 mM HEPES, adjusted to pH 7.45 with NaOH. Pipette composition: 145 mM KCl, 5 mM NaCl, 2 mM $CaCl_2$, 10 mM EGTA, 2 mM $MgCl_2$, 10 mM HEPES, adjusted to pH 7.30 with KOH.

(f) Results of Co-Culturing (i) mEC—END-2 Co-Cultures

Figure 3:
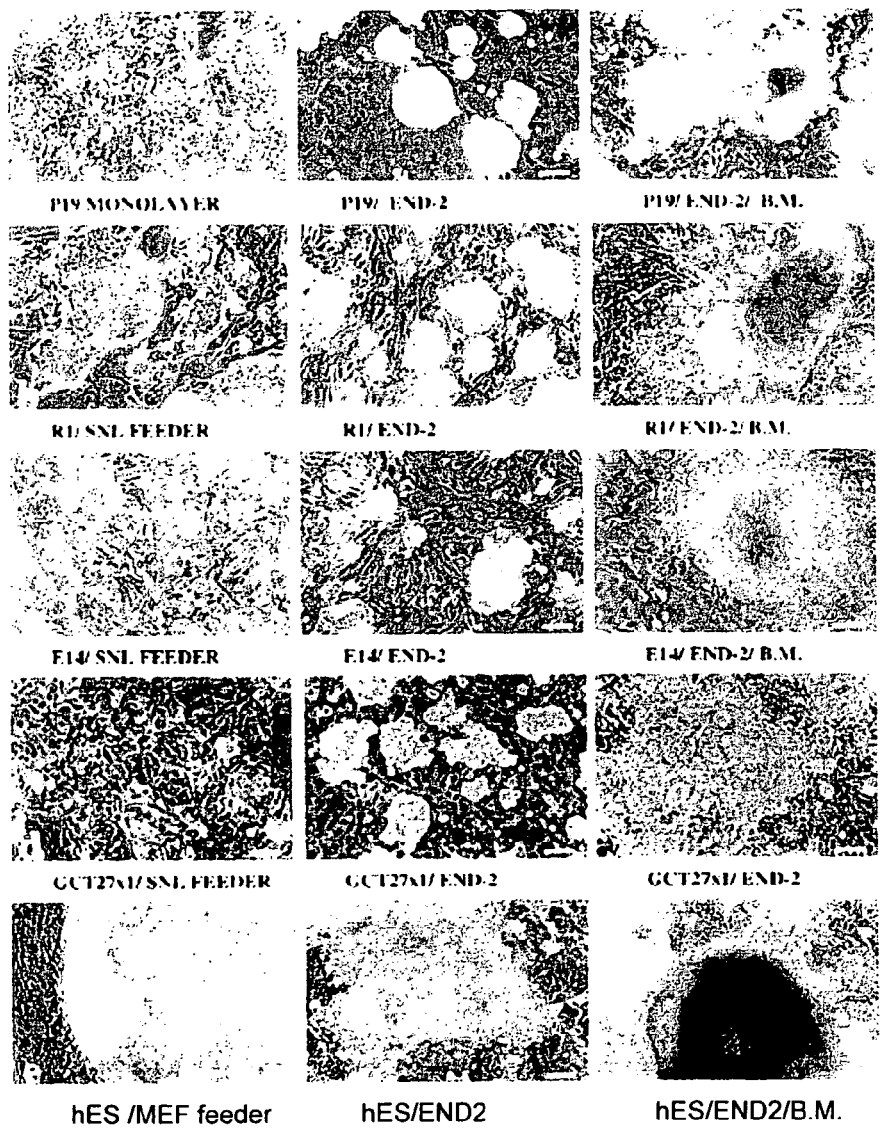
Figure 4:
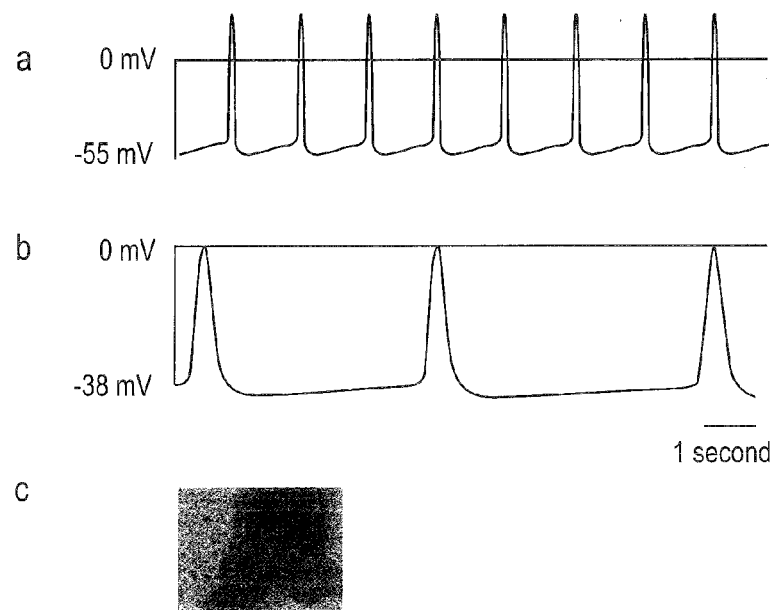

Two days after initiation of co-cultures with END-2 cells, P19 EC cells aggregated spontaneously and 7-10 days later many of the aggregates contained areas of beating muscle (FIG. 3a), as described previously (Mummery et al. 1991). Electrophysiology and RT-PCR showed that functional ion channels characteristic of embryonic cardiomyocytes were expressed in these cells (FIG. 4, Table 2).

TABLE 2

Relative levels of cardiac marker and ion channel mRNA expression as determined by semiquantitative RT-PCR. Identical amounts of cDNA of undifferentiated P19 (EC), differentiated P19 cardiomyocytes (CMC) and adult mouse heart (Heart) were PCR amplified for the indicated gene products. Relative levels for each product are indicated.

| | Ec | CMC | Heart | Ion channel and current |
|---|---|---|---|---|
| Cardiac actin | + | ++ | +++++ | |
| MLC2v+ | +++ | +++++ | | |
| a1c | + | +++ | ++++ | L-type calcium channel, $I_{ca}$ |
| Scn5a | + | + | +++++ | Heart specific sodium channel, $I_{Na}$ |
| ERG | ++ | ++ | ++++ | Delayed rectifier potassium channel, $I_{K}$. |
| Kir2.1 | − | + | ++++ | Voltage-gated potassium channel, $I_{K1}$ |
| Tubulin+++ | +++ | +++ | | |

(ii) mES—END-2 Co-Cultures

Two independent mouse ES cell lines (E14 and R1) were tested for their response to co-culture conditions. Although the cultures were not initiated as single cell suspensions, within 3 days larger aggregates than initially seeded were evident for both cell lines (FIG. 3b,c). Almost simultaneously, extensive areas of spontaneously beating cardiomyocytes were evident in the R1 ES cell cultures, although, only 7 days later, (smaller) areas of beating muscle were found in the E14 ES cells. Cells in beating areas exhibited the characteristic sarcomeric banding pattern of myocytes when stained with α-actinin (see FIG. 6d).

(iii) hEC—and END-2 Co-Cultures

The human EC cell line GCT27X is a feeder-dependent, pluripotent EC cell line, with characteristics similar to human ES cells (Pera et al. (1989), Differentiation 42, 10-23). In co-culture with END-2 cells, formation of large aggregates was observed (FIG. 3d). However even after 3 weeks, there was no evidence of beating muscle.

(iv) hES—END-2 Co-Cultures

Figure 5:
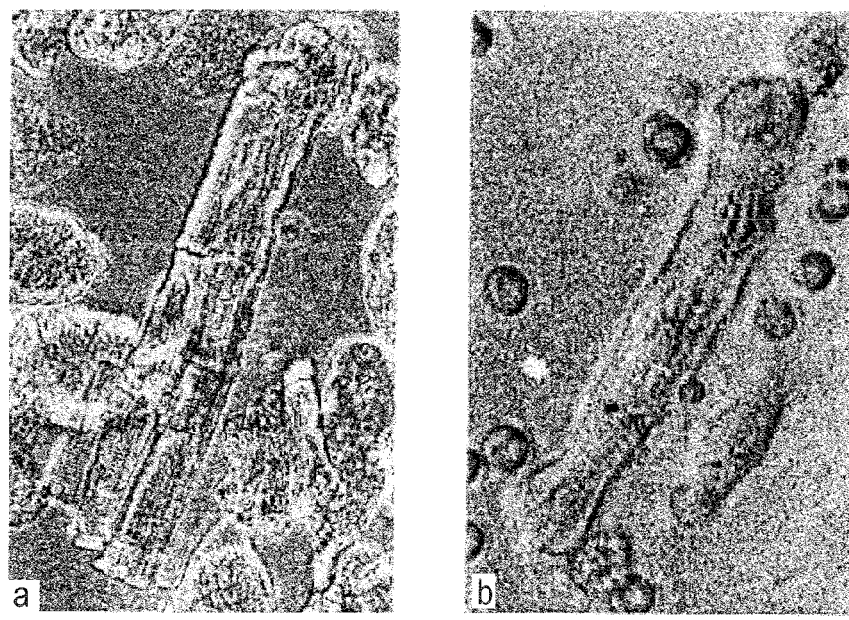
Figure 6:
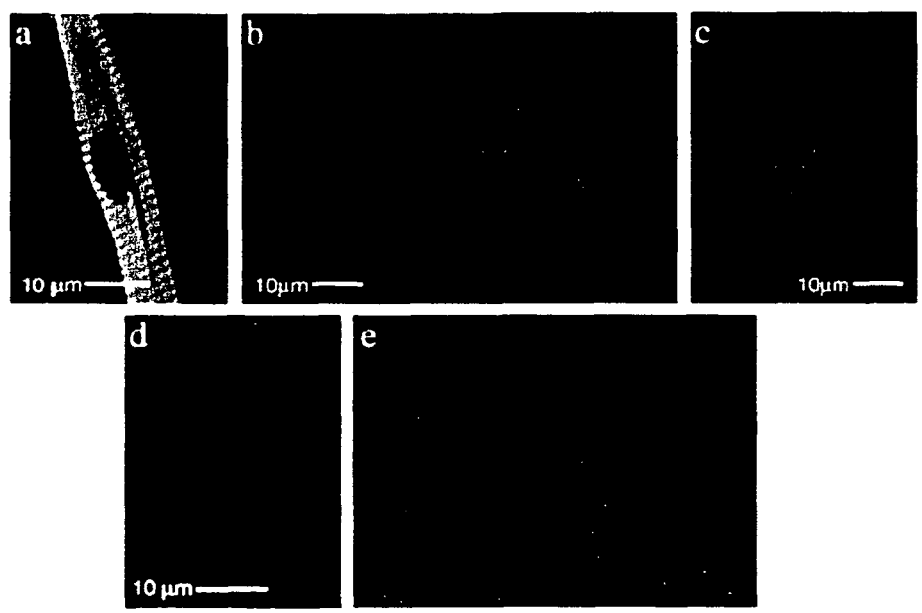

During the first week of co-culture, the small aggregates of cells gradually spread and differentiated to cells with mixed morphology but with a relatively high proportion of epithelial-like cells. By the second week, these swelled to fluid-filled cysts (not shown). Between these, distinct patches of cells become evident which begin to beat a few days later. Between 12 and 21 days, more of these beating patches appear (e.g. FIG. 3e). Overall, 15-20% of the wells contains one or more areas of beating muscle. Beating rate is approximately 60 $min^{-1}$ and is highly temperature sensitive, compared with mouse ES-derived cardiomyocytes. These cells stain positively with α-actinin, confirming their muscle phenotype (FIG. 6e). In contrast to mES and P19EC-derived cardiomyocytes, however, the sarcomeric banding patterns were poorly defined but entirely comparable with primary human cardiomycytes grown for only 2 days in culture (FIGS. 5 and 6a-c). It is clear that while primary human cardiomycytes initially retain the sarcomeric structure, standard culture conditions result in its rapid deterioration (FIG. 5). It may be assumed that hES culture conditions are not optimal for cardiomyocytes so that the hES-derived cardiomyocytes similarly exhibit deterioration in their characteristic phenotype. It will be essential to optimize these conditions to obtain fully functional cardiomyocytes from stem cells in culture. Despite deterioration in sarcomeric structure, hES derived card iomyocytes continued to beat rhythmically over several weeks and action potentials were detectable by current clamp electrophysiology (FIG. 4b), performed by inserting electrodes into aggregates, as shown in FIG. 4(c). However, carrying out electrophysiology in this manner, i.e. in aggregates rather than single cells, yields action potentials that are the accumulated effects of groups of cells. They are therefore difficult to interpret and to attribute to either ventricular, atrial or pacemaker cells. Work is currently in progress to dissociate and replate aggregates to allow single cell determinations.

(v) Cardiac Ion Channel Expression During Stem Cell Differentiation

The order in which ion currents, responsible for the subsequent phases of the adult action potential, appear during heart development has been established in electrophysiological studies (Davies et al. (1996), Circ. Res. 78, 15-25). Inward L-type $Ca^{2+}$ currents play a dominant role during early cardiac embryogenesis, whereas inward $Na^{2+}$ currents increase only just before birth (Davies et al. 1996). Mouse ES and P19 EC cells display similar timing in ion current expression (Wobus et al. (1994), In Vitro Cell. De., Biol. 30A, 425-434). To unravel the sequence of ion-channel expression at the molecular level during differentiation of P19 EC cells, we performed RT-PCR on RNA isolated from undifferentiated and 16-day-old beating clusters of P19-derived cardiomyocytes and relatively positive resting membrane potential between −40 and −60 mV (little to no IK1). These results indicate that day 16 P19 cardiomyocytes resemble fetal cardiomyocytes with respect to ion channel expression, as has been described previously for mES-derived cardiomyocytes (Doevendans et al. (1998), cardiovasc. Res. 39, 34-39).

The results of the work described here show that VE-like cells induce/promote differentiation of pluripotent cells to cardiomyocytes. These cells include pluripotent mouse EC cells, mouse ES as well as human ES cells, which are demonstrated for the first time to respond to inductive cues derived from cells similar to those normally adjacent to the region of heart development in the embryo.

Example 5

Cardiomyocyte Differentiation of Human Embryonic Stem Cells Induced by Co-Culture With Visceral Endoderm-Like Cells (a) Methods
i) Cell Culture END-2 cells and hES cells were cultured as described in Example 1. The hES2 cell line from ES Cell International Pte Ltd was used in all experiments. To initiate co-cultures, mitogenically inactive END-2 cell cultures, treated for 1 hr with mitomycin C (10 μg/ml), replaced mouse embryonic fibroblasts (MEFs) as feeders for hES cells. Co-cultures were then grown for up to 6 weeks and scored for the presence of areas of beating muscle from 5 days onwards. HepG2 cells, a carcinoma cell line resembling liver parenchymal cells (Knowles et al, (1980) Science 209:497-9), were cultured in DMEM plus 10% FCS and passaged twice weekly. Co-cultures were initiated as for END-2 cells although HepG2 do not grow as a confluent monolayer; hES cells attached preferentially to groups of HepG2. Hanging-drop cultures of P19 EC cells were initiated and maintained in DMEM/Ham's F12 (1:1), as described previously (Mummery et al, 1991), using regular FCS while bulk production of P19 embryoid bodies in the presence or absence of END-2 conditioned medium for isolation of RNA for Northern blotting, was in the presence of charcoal-stripped FCS, as described (Mummery et al, 1991) to reduce background levels of cardiomyocyte differentiation caused by lipophilic substances possibly with retinoid-like activity in FCS. P19 clone 6 were cultured in αMEM and treated αMEM conditioned by END-2 cells. For electrophysiology, beating aggregates were dissociated using collagenase and replated on gelatine-coated coverslips.

ii) Immunohistochemistry

Attached primary cardiomyocytes hES-derived cardiomyocytes were fixed with 3.0% paraformaldehyde in PBS with $Ca^+$ and $Mg^{2+}$ for 30 minutes at room temperature, then permeablized with 0.1% triton X 100 in PBS for four minutes.

Immunocytochemistry was performed by standard methods using monoclonal antibodies directed against sarcomeric proteins including α-actinin and tropomyosin (Sigma). Antibodies specific for isoforms of myosin light chain (MLC2a/2v) were used to distinguish between atrial and ventricular cells (gift of Dr. Ken Chien). Oct-4 and α1c antibodies were from Sigma. Secondary antibodies were from Jackson Immunoresearch Labs.

iii) Culture of Primary Adult and Fetal Cardiomyocytes.

Primary tissue was obtained from patients following standard informed consent procedures and approval of the ethics committee of the University Medical Centre, Utrecht. Adult cardiomycytes were isolated and cultured, as described previously (Mummery et al, (2002) J. Anat 200:233-242). Fetal cardiomycytes were isolated from fetal hearts perfused by Langendorff and cultured in a similar way with the exception the supernatant remaining after mild centrifugation contained the majority of viable cardiomyocytes that attached to laminin-coated coverslips. For electrophysiology, cells were collected in Tyrode's buffer with low calcium (Sipido et al, 1998. Cardiovasc. Res. 37:478-88) and replated directly in glass wells for patch-clamp.

iv) (Semi-Quantitative) RT-PCR

RNA was isolated using Trizol (Gibco) and reversed transcribed using M-MLV-RT (Gibco). Primers for α1c (Van Gelder et al., 1999), Kv4.3 (Calmels et al., 2001, Ref) and ANF (Kehat et al, 2001, *J. Clin. Invest.* 108, 407-414) were as described. Primers for human KvLQT1 (sense 5'-TTCTTG-GCTCGGGGTTTGCC; antisense 5'-TGTTGCTGCCGC-GATCCTTG; GenBank accession no. AF000571; product size 723 bp) and β-tubulin (sense 5'-TGGCTTTGC-CCCTCTCACCA; antisense 5'-CGGCGGAACATG-GCAGTGAA; AF141349; 369 bp) were designed using VectorNTI software (InforMax, North Bethesda, USA). Annealing temperatures and number of amplification cycles were as follows: ANF, 58° C., 35 cycles; α1c, 56° C., 38 cycles; Kv4.3 55° C., 35 cycles; KvLQT1, 58° C., 32 cycles; β-tubulin, 61° C., 30 cycles. Products were analyzed on an ethidium bromide stained 1.5% agarose gel.

v) Northern Blotting

RNA was isolated from P19 aggregates and poly A+ RNA selected, as described previously (Mummery et al, 1990, Dev. Biol. 142: 406413).

vi) Electrophysiology

Experiments were performed at 33° C., using the whole cell voltage clamp configuration of the patch clamp technique. After establishment of the gigaseal, action potentials were measured in the current clamp mode. Data were recorded from cells in spontaneously beating areas using an Axopatch 200B amplifier (Axon Instruments Inc., Foster City, Calif., U.S.A.). Output signals were digitized at 2 kHz using a Pentium III equipped with an AD/DAC LAB PC+ acquisition board (National Instruments, Austin, Tex., U.S.A.). Patch pipettes with a resistance between 2 and 4 MΩ were used. Composition of the bathing medium was 140 mM NaCl, 5mM KCL, 2 mM $CaCL_2$, 10 mM HEPES, adjusted to pH 7.45 with NaOH. Pipette composition: 145 mM KCL, 5 mM NaCL, 2 mM $CaCL_2$, 10 mM EGTA, 2 mM $MgCL_2$, 10 mM HEPES, adjusted to pH 7.30 with KOH.

(b) Cardiomyocyte Differentiation of Human ES Cells.

Figure 9A:
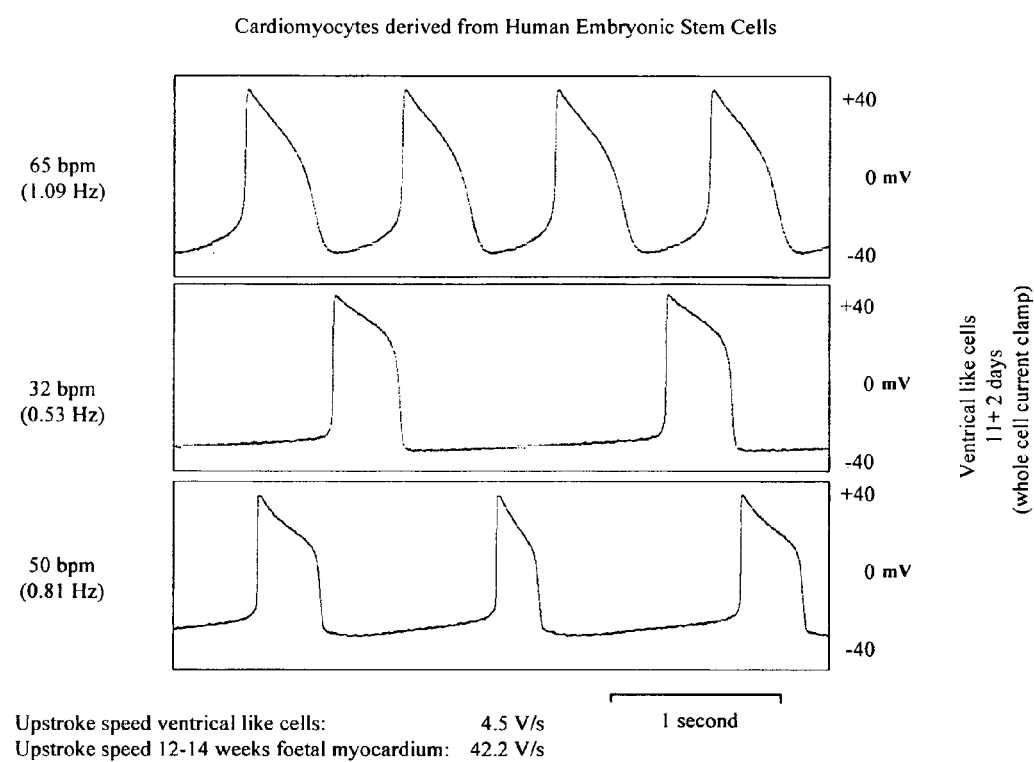
FIG. 9 shows analysis of A. action potentials and ion channels by patch clamp electrophysiology and B. real-time analysis of $Ca^{2+}$.

The majority of the experiments described here were carried out using the hES2 cell line (Reubinoff et al, 2000). The cells were maintained in an undifferentiated state by co-culture with mitomycin C-treated MEF "feeder cells" in serum-containing medium, as described (Mummery et al, 2002); under these conditions, all cells in the bulk of the culture showed nuclear staining for oct4, although any flattened cells at the edge of the culture were negative. Oct4 expression thus correlated with phenotypic characteristics of undifferentiated cells. hES cells were subcultured by transferring small clumps of undifferentiated cells either to new, mit.C-treated MEFs or confluent cultures of mit.C-treated END-2 cells. After approximately 5d under these conditions, epithelial cells became evident which over the next few days become fluid-filled cysts (FIG. 1A). These stain for alphafetoprotein, suggesting that they represent extraembryonic visceral endoderm. In addition, by 10 d areas of rhythmically contracting cells in more solid aggregates become evident (FIG. 1A, 3e) with a variety of overall morphologies (FIG. 1B, 3e). 16-35% of wells in a 12-well plate contain beating areas each of which can be dissociated and replated to yield up to 12 new colonies of beating cells with a 2-D rather than 3-D morphology; this facilitates access to the cells for further characterization by patch-clamp electrophysiology (FIG. 4, FIG. 9; see below). Both before and after dissociation, hES-derived cardiomycytes beat 45-60 times per minute, sometimes irregularly; beating was upregulated in response to pharmacological agonists such as carbachol, isoprenaline and phenylephrine.

Figure 8:
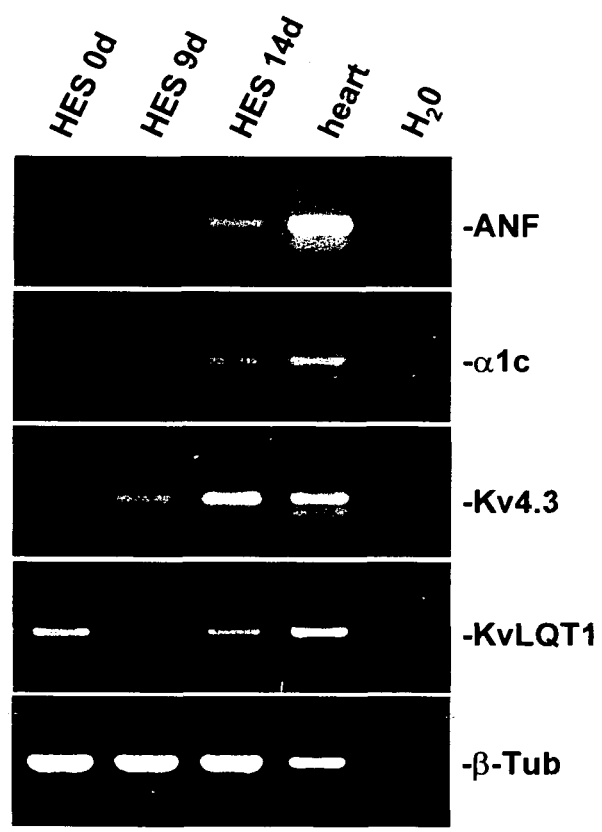
FIG. 8 shows expression of cardiomyocyte marker mRNA in co-cultures of hES and END-2 cells by RT-PCR.

In order to characterize the cardiomycytes further, immunofluorescent staining was carried out for a number of sarcomeric proteins, BIDOPY-ryonadine was used as a vital stain for sarcomeres and the expression of ion channels analysed by RT-PCR (FIG. 8). In each case, primary human fetal (17 weeks) and adult atrial and/or ventricular tissue was used as a controlled reference. The data showed that hES-derived cardiomyocytes exhibit sarcomeric striations when stained with α-actinin, organized in separated bundles (FIG. 2). These are reminiscent of the bundles observed in fetal cardiomyocytes, although the individual sarcomeres are less well defined, but are quite different from the highly organized, parallel bundles observed in ventricular cells from biopsies of adult human heart.

(c) Expression of Cardiac Ion Channels and Stem Cell/Sarcomere Markers in hES/END-2 Co-Cultures.

Expression of cardiac specific ion channels was determined in undifferentiated hES cells and in differentiating cells 9 and 14-days after initiation of co-culture with END-2 cells (FIG. 8). As shown by others previously: (Kehat et al., 2001), areas of beating hES-derived cardiomyocytes express ANF. Expression of the α-subunits of the cardiac specific L-type calcium channel (α1c) and the transient outward potassium channel (Kv4.3) are also detected, the expression of Kv4.3 preceding commencement of beating by several days. RNA for the delayed rectifier potassium channel KvLQT1 is found in undifferentiated cells, it disappears during early differentiation and reappears at somewhat later stages.

(d) Electrophysiology

Figure 9B:
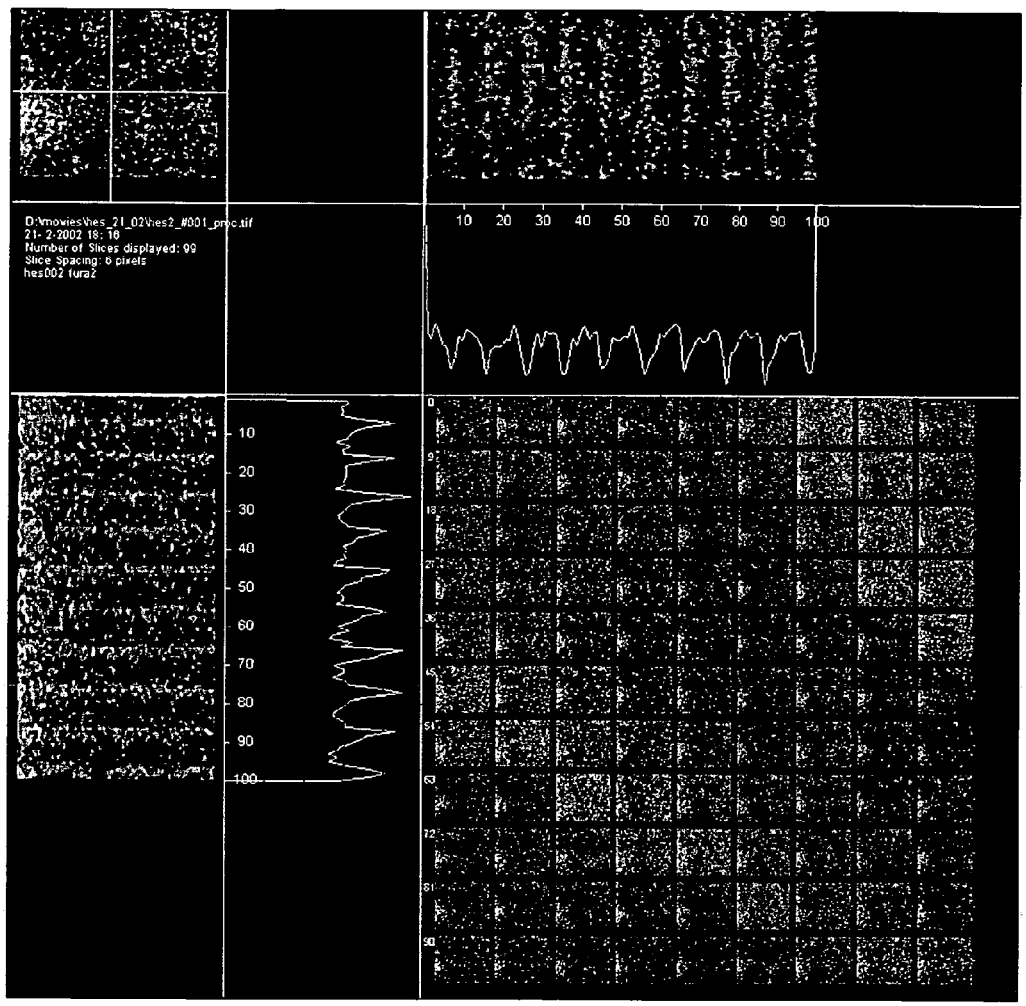

Patch clamp electrophysiology on dissociated, replated aggregates of hES cardiomyocytes showed that range of (electrical) phenotypes were present in the cultures (FIG. 9A) that were comparable with primary human cardiomyocytes of fetal origin (FIG. 9B). Ventricular-like action potentials predominated (28 of 31 determinations) but both atrial and pacemaker-like cells were also present (2 and 1 of 31 determinations, respectively). Of note was the relatively slow upstroke velocity (7.0+/−0.8 V/s) and low membrane potential (FIG. 9A), indicating that cells were relatively immature even compared with fetal human cardiomyocytes of 17 weeks gestation. In areas of co-culture in which the cells were not beating but had adapted morphologies indistinguishable from beating areas, current injection was sufficient to induce repeated action potentials and sustained rhythmic contractions. In addition co-cultures of hES cells with HepG2 cells resulted cardiomyocytes with action potentials similar to those in hES-END-2 co-cultures.

Calcium transients in groups of beating hES cardiomyocytes were also determined in real time using Fura-2, for which the fluorescence emission spectrum depends on the intracellular calcium concentration. FIG. 9B shows that repetitive $Ca^{2+}$ transients are generated in hES cardiomyocytes, reflecting their ability to beat in the absence of obvious conductance cells.

(e) Effects of END-2 Conditioned Medium on Aggregates of P19EC Cells.

Figure 10A:
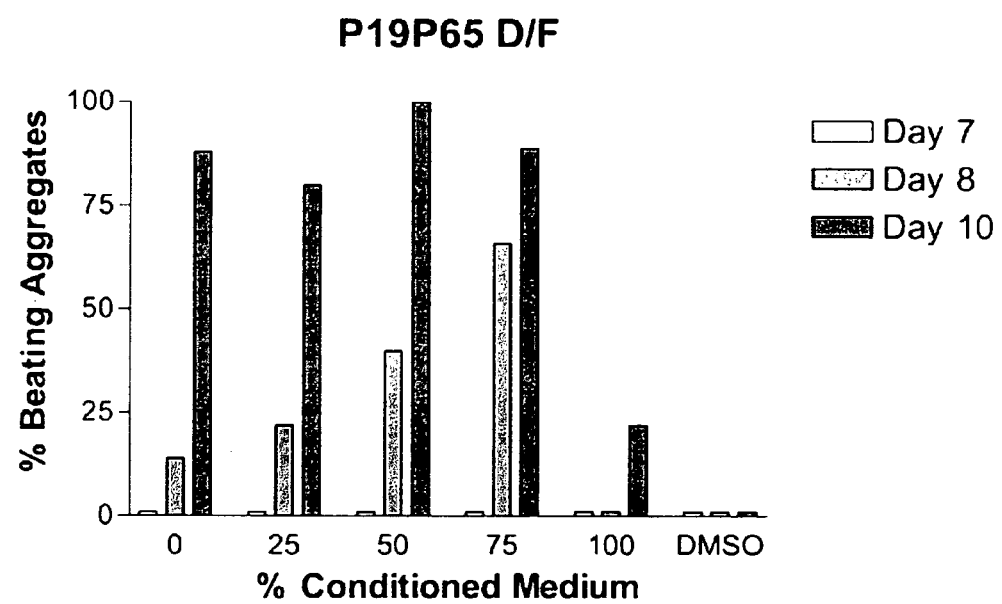
Figure 10B:
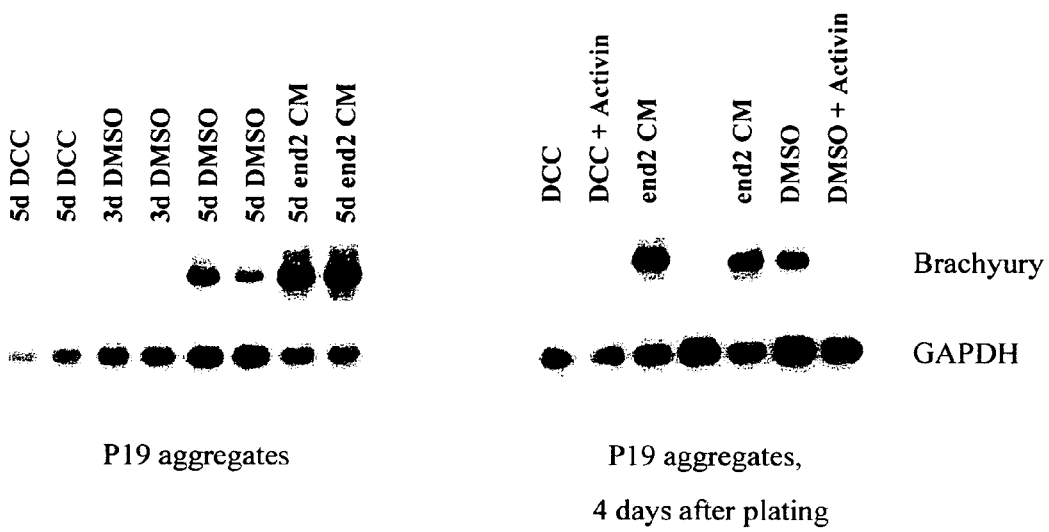

We have shown previously (Mummery et al, 1991) that medium conditioned for 24 h by END-2 cells can induce their differentiation so that within 10 days nearly all aggregates replated after 3d growth as hanging drops, contain beating muscle. In the presence of regular FCS, differentiation is significantly enhanced above background levels. Background differentiation levels are reduced virtually to zero if the FCS is passed over an activated charcoal column (DCC-FCS) to remove residual retinoids; in addition, differentiation is blocked by activin (van den Eijnden-van Raaij et al, 1991, Mech. Dev. 33:157-166). END-2-CM was tested on both hES and mES cells cultured on MEFs (without MEFs the cells die/differentiate in a non-directed way) but failed to override any differentiation inhibiting activity secreted by MEFs. The P19EC assay system was preferred because these cells are feeder independent for undifferentiated growth. These experiments show that the END-2 CM has a dose dependent effect in promoting the appearance of cardiomyocytes in replated aggregates in two independent clones of P19 EC cells (FIG. 10A). More importantly, the effect appears to be related to an early effect on the differentiation of nascent mesoderm; Northern blot analysis shows that END-2 CM upregulates an early mesoderm marker Brachyury T (Hermann, 1991) in the aggregation phase during the first 3 days (FIG. 10B), that levels are maintained immediately after plating but that after 9 days, Brachyury T is no longer detectable. Moreover, the induction of Brachyury T is blocked by the additional presence of activin (FIG. 10B), consistent with its ability to block the formation of beating muscle in aggregates. The transient expression of Brachyury T is similar to that observed during early mesoderm differentiation during gastrulation of the mouse embryo.

Control of sustained growth and the ability to induce specific differentiation pathways are essential if human embryonic stem (hES) cells are to reach their potential in the treatment of disease by cell transplantation therapy.

IT is therefore shown that co-culture of hES cells with visceral endoderm-like cells from the mouse initiates a differentiation programme that leads to the formation of beating muscle cells. Expression of sarcomeric marker proteins and ion channels demonstrates these cells are cardiomyocytes, while patch-clamp electrophysiology on single cells demonstrates that the majority is ventricular in phenotype. This system provides a model for the study of human cardiomyocytes in culture, generally difficult to achieve, and perspectives for cardiomyocytes transplantation therapies where it is envisaged that replacement of ventricular cells lost in ischemic heart disease will help restore cardiac function. This is the first demonstration of the induction of cardiomyocyte differentiation in a hES cell line that does not undergo spontaneous differentiation to somatic lineages.

Example 6

Myocardial Infarction Model in Mice

In order to test the ability of stem-cell-derived cardiomyocytes to restore cardiac function, a MI model has been developed in mice. In pentobarbital anesthetized adult mice, the chest is opened through a midsternal approach. The anterior descending branchis identified and ligated. Successful procedures induce a discoloration of the distal myocardium. The chest is closed with three sutures and the animal is allowed to recover. In total, 17 animals have been operated on. Seven received a sham procedure including positioning of the suture and 10 were ligated. Four weeks after MI the mice were anaesthetized again using the same medication by intraperitoneal injection. For the haemodynamic study the animals were incubated, and connected to a rodent respirator (Hugo Sachs Electronics, March—Hugstetten Germany). Instrumentation was performed with the chest closed by introducing a catheter into the jugular vein.

Figure 7:
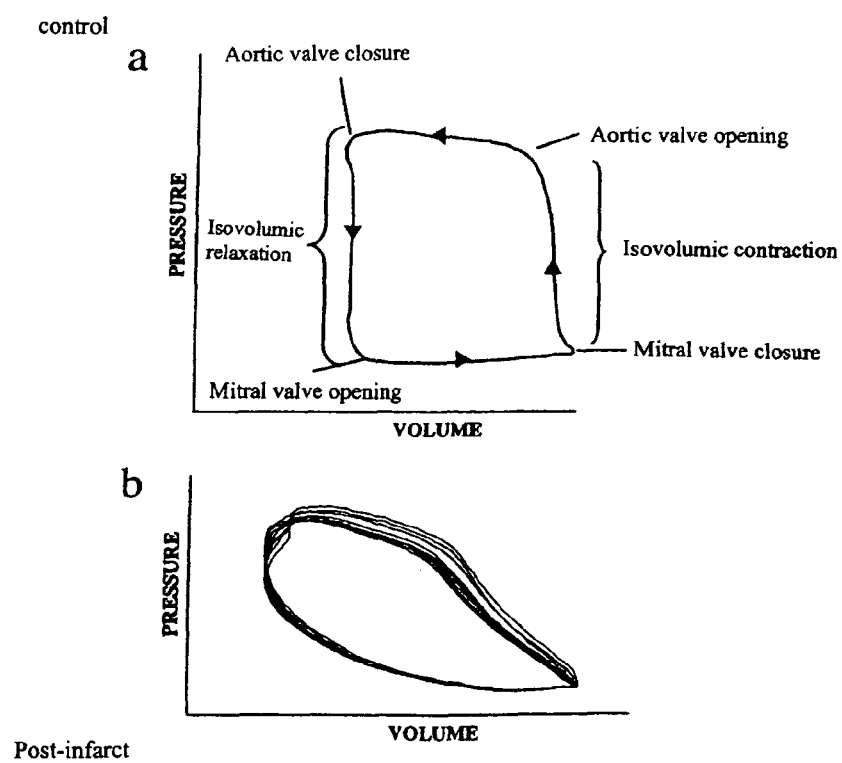

A 1.4 French conductance-micromanometer (Millar Instruments, Houston, Tex., USA) was delivered to the left ventricle through the carotid artery. Pressure and conductance measurements were recorded using Sigma SA electronic equipment (CDLeycom, Zoetermeer, the Netherlands) and stored for offline analysis. A typical pressure volume (PV) loop recorded in a normal heart is presented in FIG. 7(a). From the PV-loops many haemodynamic parameters can be deduced including the end-systolic PV relationship (ESPVR) and preload recruitable stroke work (PRSW).

Finally, the invention as hereinbefore described is susceptible to variations, modifications and/or additions other than those specifically described and it is understood that the invention includes all such variations, modifications and/or additions which may be made it is to be understood that various other modifications and/or additions which fall within the scope of the description as hereinbefore described.

The invention claimed is:

1. A method of inducing differentiation of an human embryonic stem (hES) cell into a mesodermal cell, said method comprising:
culturing the hES cell in the presence of an embryonic cell and/or extracellular medium of an embryonic cell for a sufficient amount of time to induce differentiation of the hES cell into a mesoderm cell, wherein said embryonic cell is an endodermal or ectodermal cell, and said mesoderm cell is a cardiomyocyte or vascular endothelial cell.

2. A method of obtaining a subpopulation of mesoderm cells in vitro comprising inducing the differentiation of a population of hES cells according the method of claim 1.

3. A method according to claim 1 where the embryonic cell is an endodermal cell.

4. A method according to claim 1, wherein the embryonic cell is obtained from visceral endoderm tissue.

5. A method according to claim 4, wherein the visceral endoderm tissue is obtained from an early post-gastrulation embryo.

6. A method according to claim 1 or 2 further comprising: pre-culturing the embryonic cell to form an embryonic cell monolayer; and co-culturing the hES cell in the presence of the embryonic cell monolayer and/or extracellular media of the embryonic cell monolayer.

7. A method according to claim 6, wherein the hES cell and embryonic cell monolayer are separated by a filter or a cellular matrix.

8. A method according to claim 1 or 2, wherein the mesoderm cell is a vascular endothelial cell.

9. A method according to claim 1 or 2, wherein the mesoderm cell is a cardiomyocyte.

10. A method according to claim 9, wherein the
embryonic cell is a visceral endoderm cell and the mesoderm cell is a cardiomyocyte.

11. A method according to claim 1, wherein the embryonic cell is obtained from extraembryonic ectoderm and/or endoderm tissue.

12. A method according to claim 11, further including culturing the embryonic stem cell in the presence of VEGF.

13. A method according to claim 1 or 2, wherein the hES cell is genetically modified.

14. A method according to claim 2, wherein the subpopulation consists essentially of cardiomyocytes.

15. The method of claim 4, wherein said embryonic cell expresses alpha-feto protein.

16. A method according to claim 1, wherein the embryonic cell is an END-2 cell.

17. A method according to claim 6, wherein the embryonic cell is an END-2 cell.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 1
ccagatgaga cccgcagcgt aa         22

<210> SEQ ID NO 2
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 2
gtctgcggcg ttctccatct c          21

<210> SEQ ID NO 3
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 3
cttggccaag atcaacctgc tct        23

<210> SEQ ID NO 4
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 4
cggacagggc caaatactca atg        23

<210> SEQ ID NO 5
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 5
tcactgtgcc tgaacttacc            20

<210> SEQ ID NO 6
<211> LENGTH: 19

```
<212> TYPE: DNA
<213> ORGANISM: Artificial Sequence
<220> FEATURE:
<223> OTHER INFORMATION: oligonucleotide primer

<400> SEQUENCE: 6
gaacatagcc gtaaactgc                                              19

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
ttcttggctc ggggtttgcc                                             20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
tgttgctgcc gcgatccttg                                             20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
tggctttgcc cctctcacca                                             20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
cggcggaaca tggcagtgaa                                             20
```